(12) United States Patent
Smith

(10) Patent No.: US 7,335,207 B1
(45) Date of Patent: Feb. 26, 2008

(54) MINIMALLY INVASIVE CUP IMPACTOR

(75) Inventor: Aaron Smith, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 533 days.

(21) Appl. No.: 10/722,627

(22) Filed: Nov. 26, 2003

(51) Int. Cl.
*A61B 17/58* (2006.01)
(52) U.S. Cl. .............. 606/99; 606/80; 606/81
(58) Field of Classification Search ............ 606/79–81, 606/91, 99, 100; 623/22.21–22.39
See application file for complete search history.

(56) References Cited

U.S. PATENT DOCUMENTS

| | | | |
|---|---|---|---|
| 1,199,823 A * | 10/1916 | Sadtler ................ 81/57.29 |
| 1,677,337 A | 7/1928 | Grove | |
| 1,866,714 A * | 7/1932 | King .................... 408/127 |
| 2,526,105 A | 10/1950 | Adams | |
| 3,232,151 A | 2/1966 | Blachowski | |
| 3,696,694 A | 10/1972 | Boro | |
| 3,859,992 A * | 1/1975 | Amstutz ................ 606/91 |
| 4,065,941 A | 1/1978 | Aoki | |
| 4,114,401 A | 9/1978 | Van Hoose | |
| 4,305,394 A * | 12/1981 | Bertuch, Jr. ............. 606/91 |
| 4,362,520 A * | 12/1982 | Perry ................... 464/149 |
| 4,475,549 A | 10/1984 | Oh | |
| 4,528,980 A | 7/1985 | Kenna | |
| 4,632,111 A * | 12/1986 | Roche ................... 606/53 |
| 4,781,181 A * | 11/1988 | Tanguy .................. 606/64 |
| 4,936,701 A | 6/1990 | Allen et al. | |
| 4,970,918 A | 11/1990 | Brewer et al. | |
| 5,061,270 A * | 10/1991 | Aboczky ................ 606/91 |
| D331,461 S | 12/1992 | Lester | |
| 5,364,403 A | 11/1994 | Petersen et al. | |
| 5,431,657 A * | 7/1995 | Rohr .................... 606/91 |
| 5,474,560 A | 12/1995 | Rohr, Jr. | |
| 5,540,697 A * | 7/1996 | Rehmann et al. .......... 606/91 |
| 5,584,837 A * | 12/1996 | Petersen ................ 606/91 |
| 5,683,399 A | 11/1997 | Jones | |
| 5,738,586 A | 4/1998 | Arriaga | |
| 5,797,918 A | 8/1998 | McGuire et al. | |
| 5,902,107 A * | 5/1999 | Lowell ................. 433/130 |
| 5,925,077 A * | 7/1999 | Williamson et al. ..... 623/22.34 |
| 6,390,927 B1 | 5/2002 | Cleveland, III | |
| 7,004,946 B2 * | 2/2006 | Parker et al. ............ 606/99 |
| 7,037,310 B2 * | 5/2006 | Murphy ................. 606/91 |
| 2002/0049500 A1 | 4/2002 | Draenert | |
| 2003/0229356 A1 * | 12/2003 | Dye ..................... 606/99 |

\* cited by examiner

*Primary Examiner*—Eduardo C. Robert
*Assistant Examiner*—James L Swiger
(74) *Attorney, Agent, or Firm*—Harness, Dickey & Pierce, P.L.C.

(57) ABSTRACT

A method and apparatus for implanting a prosthetic through a less invasive procedure. Generally, an instrument is provided to allow for a torque transfer along a non-linear line. Therefore, an incline can be provided without obstructing the view of a user using the instrument.

28 Claims, 6 Drawing Sheets

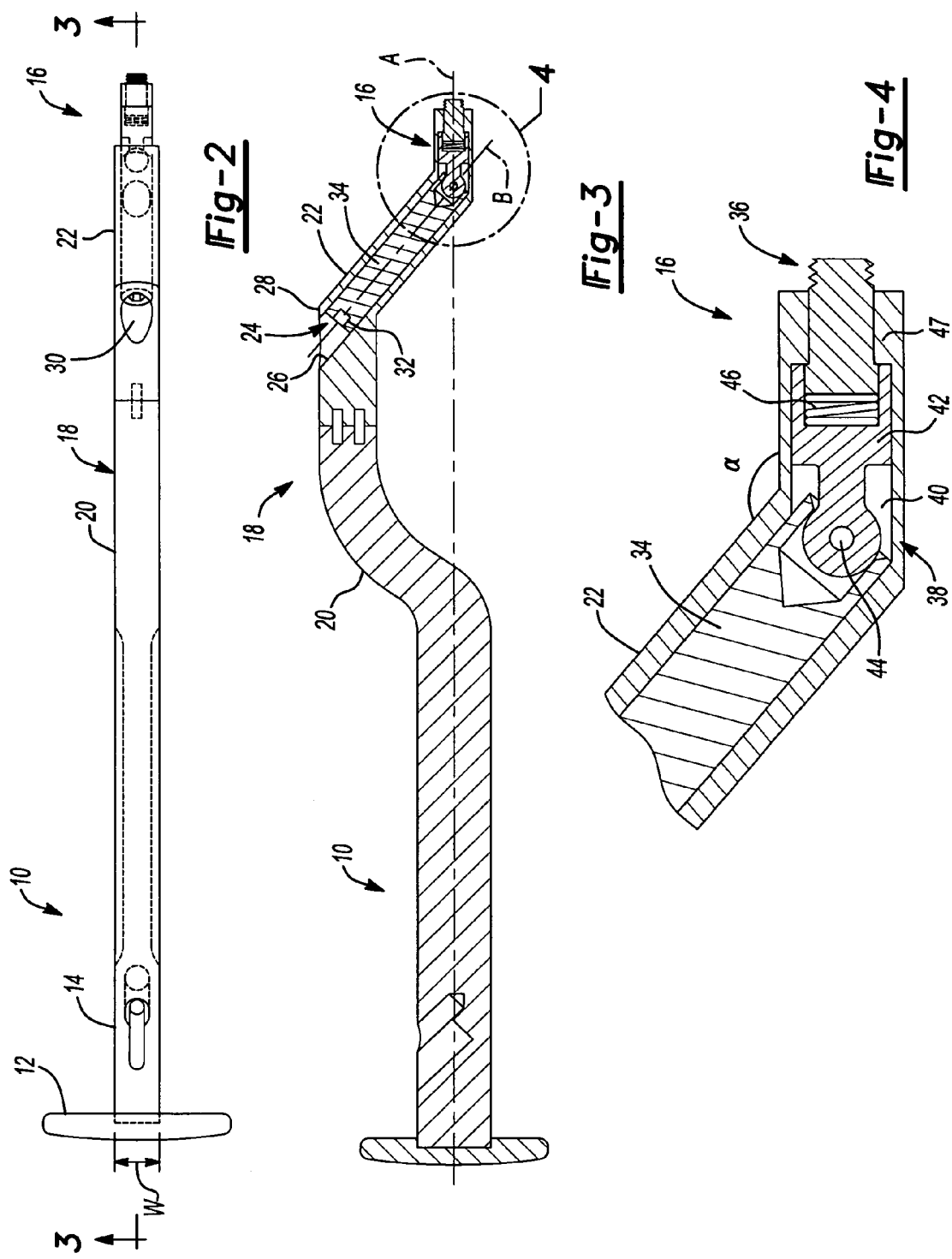

us 7,335,207 B1

MINIMALLY INVASIVE CUP IMPACTOR

FIELD

The present invention relates generally to orthopedic surgical procedures and instruments, and particularly to methods and apparatuses for implanting a cup.

BACKGROUND

Various procedures may be performed to implant prosthetics in an anatomy, such as a human anatomy, to assist in regaining substantially normal or anatomical movement of a selected portion. For example, in a natural anatomy a hip joint is formed by the articulation of the head of the femur with an acetabulum defined by the pelvis. Nevertheless, due to various reasons, such as injury, age, and other deteriorations, the acetabulum may no longer articulate smoothly with the head of the femur at a particular time. Therefore, it may be desirable to replace the acetabulum with an appropriate implant to allow for substantially natural articulation of the head of the femur with the acetabular implant.

A large incision may be formed in the dermis of a patient to gain access to a selected joint, such as a hip joint, to provide the selected implant thereto. In addition, the femoral head must often be dislocated from the acetabulum to provide an implant to the acetabulum. Such procedures may cause trauma to the patient in addition to the trauma required by the procedure to implant the selected implants. Therefore, it is generally desirable to decrease trauma during a procedure required to implant a selected implant.

For example, such as with an acetabulum cup, it is necessary to implant the cup into a generally confined area, therefore requiring maximum visibility through a less invasive procedure. Therefore, it is desirable to provide instruments that allow for maximum visibility through a less invasive incision so that the precise work of the implantation can occur without increasing trauma to the patient.

SUMMARY

A method and apparatus for providing an implant into a body for a selected purpose. For example, an impactor may be used to implant an acetabular cup into a prepared acetabulum of an individual. Generally, the impactor includes an offset or angled portion, such that a portion exterior to the patient is not in a direct line of sight with the implantation site within the patient.

Mechanisms, such as a threaded member, generally engage an acetabular cup implant during the implantation procedure. A torque transfer mechanism is provided to transfer torque through the offset portion to disengage the acetabular implant after implantation of the acetabular implant. Various mechanisms, such as flexible coils, universal joints, and similar techniques are provided to allow for the transfer of torque from a first plane to a second plane, such that an implant can be disengaged from an implant instrument through a substantially less invasive incision.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 2 is a top plan view of the instrument in FIG. 1;

FIG. 3 is a cross-sectional view taken along line 3-3 of FIG. 2;

FIG. 4 is a detailed cross-sectional view of the circle in FIG. 3;

DETAILED DESCRIPTION OF VARIOUS EMBODIMENTS

The following description of various embodiments is merely exemplary in nature and is in no way intended to limit the invention, its application, or uses. Although the following description relates generally to the implantation of an acetabular cup into a prepared acetabulum of an individual, it will be understood that the described instruments and methods may be used for any appropriate procedure. For example, a similar instrument may be used to impact or implant a glenoid implant or various articulate surfaces of other bones, such as a tibia and a humerus. Therefore, it will be understood that the following discussions is not intended to limit the scope of the appended claims.

Figure 1:
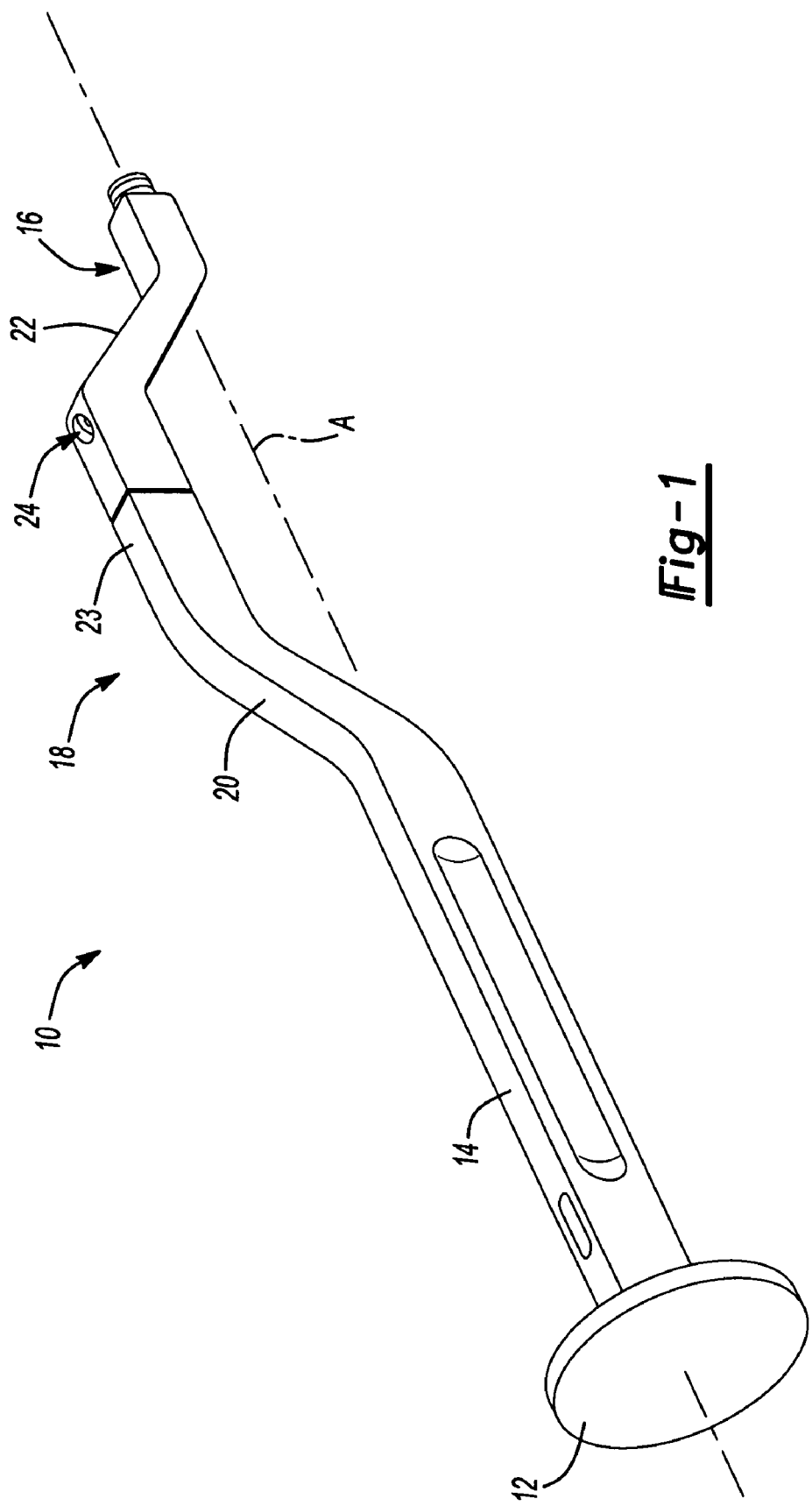
FIG. 1 is a perspective view of an instrument according to an embodiment.

With reference to FIG. 1, an impactor 10 is illustrated. The impactor 10 may be used to impact an acetabular cup, as described herein, into a prepared acetabulum of a patient. Those skilled in the art will also understand that the impactor 10 may be used to impact other implants as well. Nevertheless, the impactor 10 generally includes an impactable or strikable head 12 extending from a graspable portion 14 that is generally aligned with a positioning and holding portion 16. The positioning portion 16 is aligned along an axis or plane A, with the graspable portion 14. Disposed between the graspable portion 14 and the positioning portion 16 is an angled or clearance portion 18. The clearance portion 18 includes a proximal end 20 that extends from the graspable portion 14 and a distal end 22 that extends from the positioning portion 16. A parallel portion 23 extends between the proximal portion 20 and the distal portion 22. The parallel portion 23 is generally parallel to and spaced from the axis A. The proximal portion 20 and distal portion 22 allow for the clearance portion 18 to be positioned away from the axis A to allow for viewing of an operating area, as described herein.

The impactor 10 may be formed of any appropriate material. Generally, the impactor 10 will be subjected to forces as the impactor 10 is struck to impact the acetabular cup. Therefore, metals or biocompatible alloys, such as stainless steel, titanium, and other appropriate materials, may be used to form the impactor 10. Nevertheless, it will be understood that appropriately reinforced polymers and other materials may also be used to form the impactor 10.

With continuing reference to FIG. 1 and additional reference to FIGS. 2 and 3, a width W of the impactor 10 is generally selected to be substantially narrow. Therefore, the width W of the impactor 10 may not obstruct viewing of an area near the positioning portion 16 of the impactor 10. Although the impactor 10 is illustrated to include substantially flat sides, it will be understood that the impactor 10 may also be generally rounded or oval in shape and generally shaped to provide rigidity for the impaction of the acetabular cup, as is described herein.

With continuing reference to FIGS. 1-3, a torquing or torque transfer mechanism 24 is provided or disposed in a bore 26 defined by a portion of the distal member 22. The torquing mechanism 24 allows a torque to be transferred from a point distal or away from the positioning portion 16. As illustrated here, the point where the torque is initiated is generally near a proximal end 28 of the distal portion 22 of the extending portion 18. The bore 26 extends through the impactor 10 to form the aperture 30. The aperture 30 allows a tool 430 (FIG. 11) to engage a tool engagable portion 32 of the torque transfer mechanism 24, such that the tool may rotate the first portion 34 of the torque transfer mechanism 24.

The initial portion or rod 34 of the torque transfer mechanism 24 is generally interconnected with a threaded member 36 of the positioning portion 16. The rod 34 is interconnected with the threaded member 36 through a universal ball joint 38. The universal ball joint 38 includes a ball member 40 that extends from a threaded engaging member 42. The universal ball joint 38 may interconnect the threaded member 36 and the rod 34 in any appropriate manner. For example, a pin 44 may be provided through the ball 40 to engage a selected portion of the rod 34. Therefore, a torque from the rod 34 would be transferred through the pin 44 into the ball 40. Nevertheless, the ball 40 would allow the rod 34 to rotate regardless of an angle α defined by the distal portion 22 and the positioning portion 16.

The threaded member 36 is operably engaged to the threaded member engaging portion 42 through an appropriate mechanism, such as a generally known hex engagement. A spring 46 may also be positioned near the threaded member 36. In particular, the spring 46 is operable to be positioned between the threaded member 36 and the threaded member engaging portion 42. As discussed herein, an implant, such as an acetabular cup (400 in FIG. 9) can be implanted with the instrument 10. The spring 46 can minimize the force applied to the implant 400 with the threaded member 36 rather than an exterior or driving portion 47 of the instrument 10. Therefore, the force may be applied to the implant 400 without potentially stripping or otherwise damaging the threads.

The universal ball joint 38 illustrated in FIGS. 3 and 4, is an exemplary embodiment of a mechanism to allow transfer of torque from a first plane or axis B to the second plane A. Generally, the plane A is angled, at about the angle α, relative to the axis B along which the torque may be initiated. That is the positioning portion 16 is generally in a small or enclosed area that is angled relative to the clearance portion 18. Therefore, to provide torque to the positioning portion 16, and particularly the threaded member 36, torque must be first applied at a position distal or away from the threaded member 36. Therefore, the impactor 10 includes the torque transfer mechanism 24 to transfer torque from the axis B to the axis A to engage and disengage a selected component. Although the universal ball joint 38 is an exemplary embodiment, it will be understood that any other appropriate mechanism may be used to define the torque transfer mechanism 24.

Figure 5:
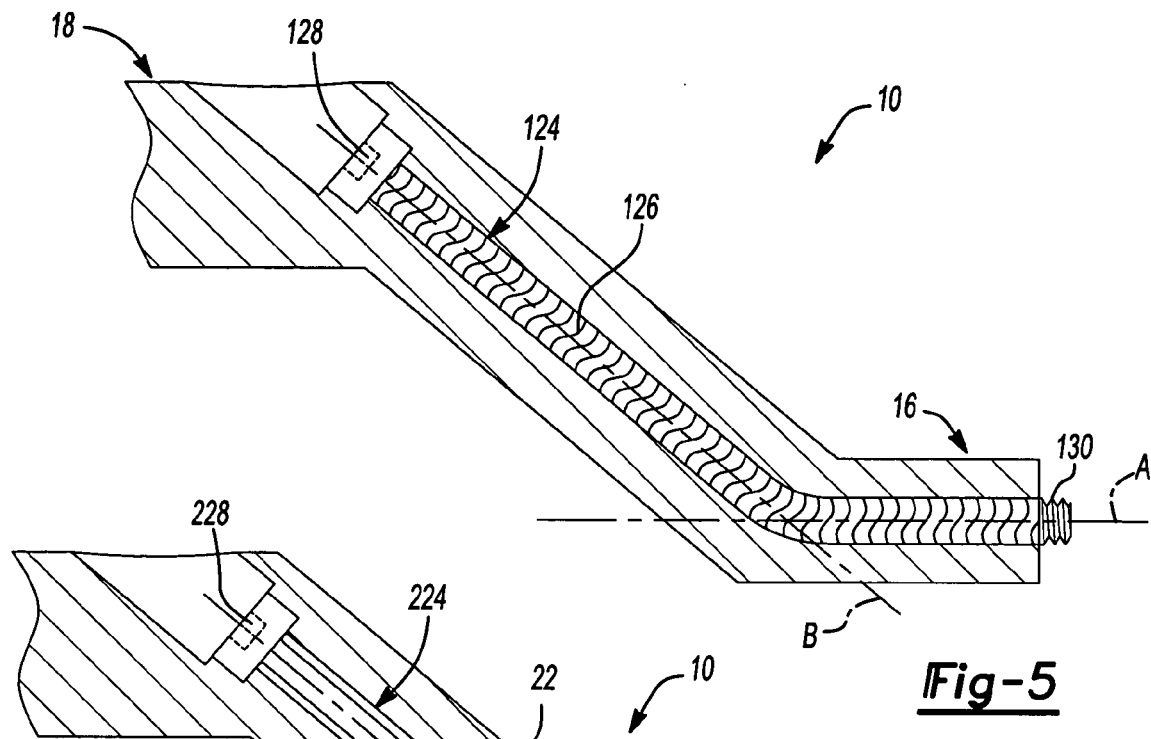
FIG. 5 is a cross-sectional view of an instrument according to an alternative embodiment.

For example, with reference to FIG. 5, a second exemplary torque transfer mechanism 124 is illustrated. Similar elements to those illustrated in FIGS. 1-4 are given the same reference numerals for ease of discussion. The impactor member 10 includes the first axis A, which aligns the positioning portion 16 and the graspable portion 14. The second or torque initiation axis B is generally provided at a selected angle relative to the axis A.

The torque transfer mechanism 124 may include a flexible torque transfer cord 126. The torque transfer cord 126 may include a tool engaging portion 128 that extends relative to the clearance portion 18. The flexible cord 126 is generally flexible enough to flex between the axis B and the axis A. A threaded member 130 extends from an end thereof or may engage the chord 126. The flexible braid 126 is generally stiff enough that a torque provided at the tool engaging end 128 is substantially transferred through the threaded member 130. Therefore, although the braided member 126 is able to flex at the angle between the axis A and the axis B, the corded member 126 is able to transfer a torque along its length. Therefore, the bore 26 defined by the distal portion 22 is able to receive the braided cord 126 as the torque transfer mechanism 124.

Figure 6:
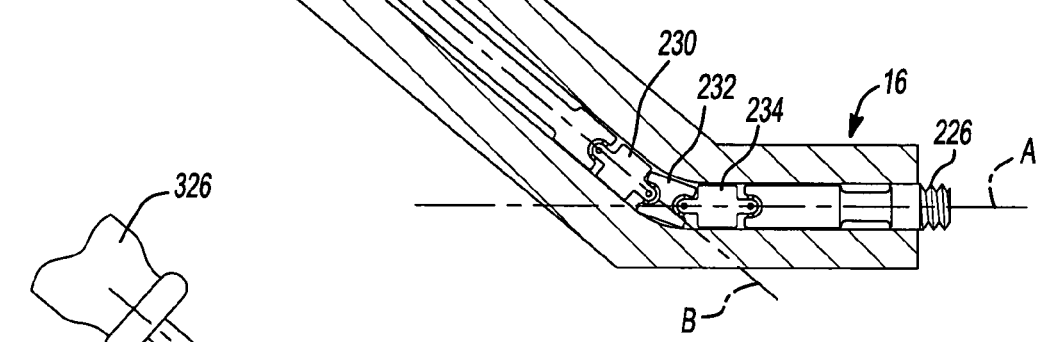
FIG. 6 is a cross-sectional view of an instrument according to an alternative embodiment.

With reference to FIG. 6, a further alternative torque transfer mechanism 224 may be provided in the distal portion 22 of the impactor 10. Again, similar numerals reference like portions as described above. The torque transfer mechanism 224 operably engages a threaded member 226. The torque transfer mechanism 224 also includes a tool engaging portion 228. The tool engaging portion 228 allows a tool to engage the torque transfer mechanism 224 to transfer torque through the threaded member 226. Again, the torque transfer mechanism 224 is generally positioned in the distal portion 22 that extends along axis B and the threaded member 226 is provided in the positioning portion 16 that is generally aligned along axis A. Therefore, the torque transfer mechanism 224 allows torque to be transferred from along axis A to along axis B.

The torque transfer mechanism 224 includes a universal linkage that may include any appropriate number of links, but generally includes a proximal link 230, a middle link 232, and a distal link 234. The links are interconnected to allow relative movement, one to another, in any appropriate manner. The plurality of links 230, 232, and 234 are generally provided so that they may bend around the angle, defined between axis A and axis B, yet rigid enough to transfer a torque applied along axis B to axis A and the threaded member 226.

Figure 7:
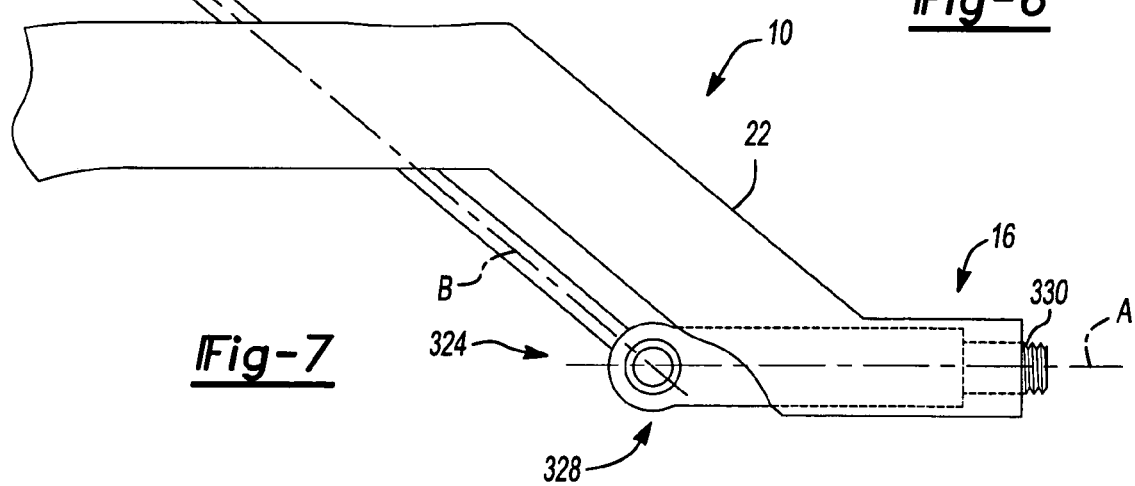
FIG. 7 is a cross-sectional view of an instrument according to an alternative embodiment.

With reference to FIG. 7, the impactor 10 may include a torque transfer mechanism 324 that may include a tool or instrument 326 that is able to engage with a tool engaging portion 328 extending proximally from the positioning portion 16. The tool engaging portion 328 is generally positioned along the axis A of the impactor 10, while the tool 326 is positioned along axis B of the distal extending portion 22. Nevertheless, the instrument 326 is able to generally directly engage the tool engaging portion 326, which engages a threaded member 330 that is able to engage the acetabular cup. The torque transfer mechanism 324 includes the instrument 326 and is able to engage the threaded member 330. A mechanism is not substantially provided in the distal extending portion 22, but the instrument extends therealong. Therefore, it will be understood that providing a torque transfer mechanism that is disposed completely within the impactor 10 is not necessary.

Figure 8:
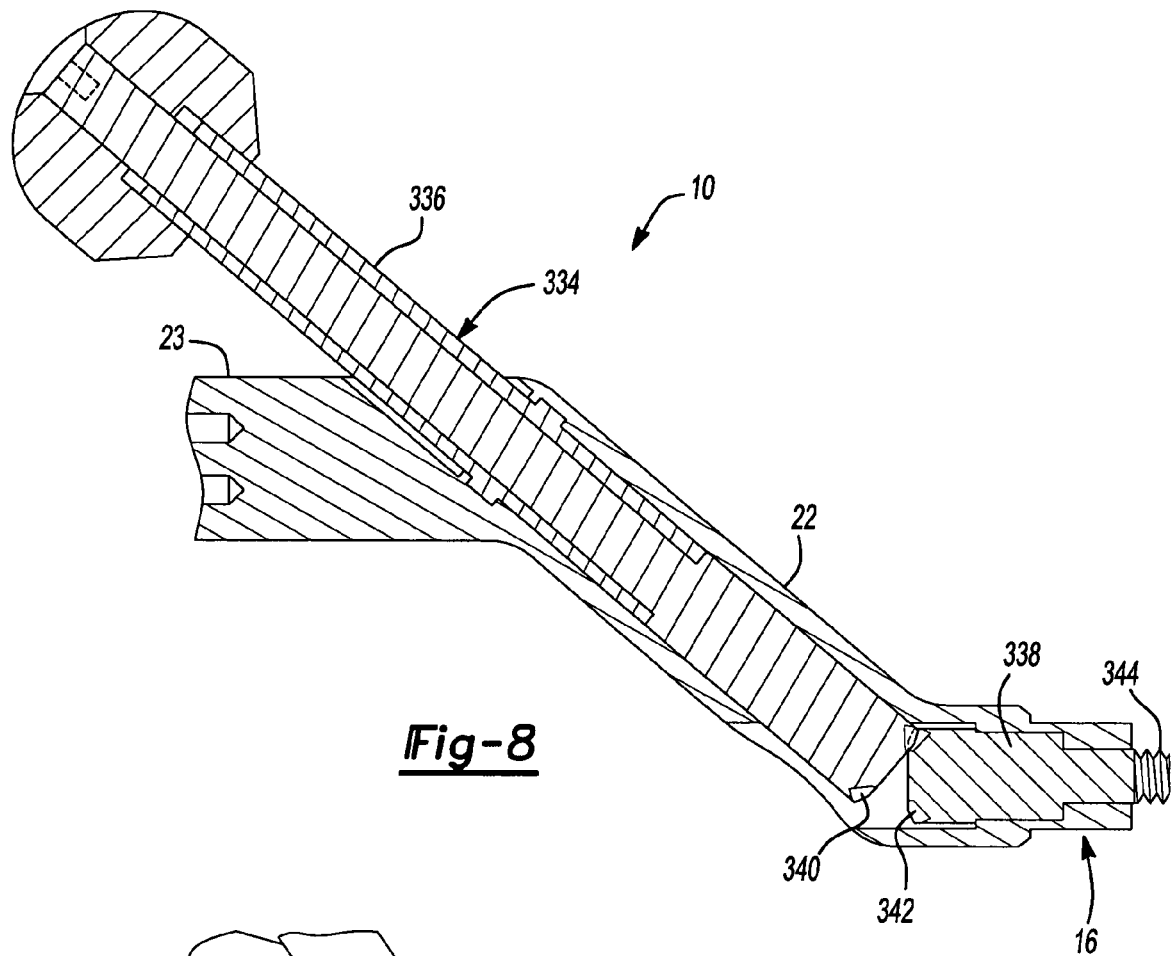
FIG. 8 is a cross-sectional view of an instrument according to an alternative embodiment.

With reference to FIG. 8, the impactor 10 may include a torque transfer mechanism 334 according to various embodiments. The torque transfer mechanism 334 generally extends through the distal end 22 that extends from the generally parallel portion 23. The torque transfer mechanism 334 generally includes a torque initiation or driving portion 336 and a torque receiving or transferring portion 338. An end of the torque initiation portion 336 defines a plurality of teeth 340 such as in a gear. An end of the torque transfer portion 338 also defines a plurality of complimentary teeth 342. The first set of teeth 340 and the second set of teeth 342 are generally complimentary such that they are able to intermesh such that one may move the other in a selected manner.

Therefore, as the torque initiation member 336 is rotated, the first set of teeth 340 engage the second set of teeth 342 to rotate the torque transfer member 338. This is regardless that the torque initiation member 336 is generally positioned at an angle relative to the torque transfer mechanism 338. An exemplary gear mechanism includes a mitre gear formation which allows the angled intermeshing of the first set of teeth 340 and the second set of teeth 342.

Figure 9:
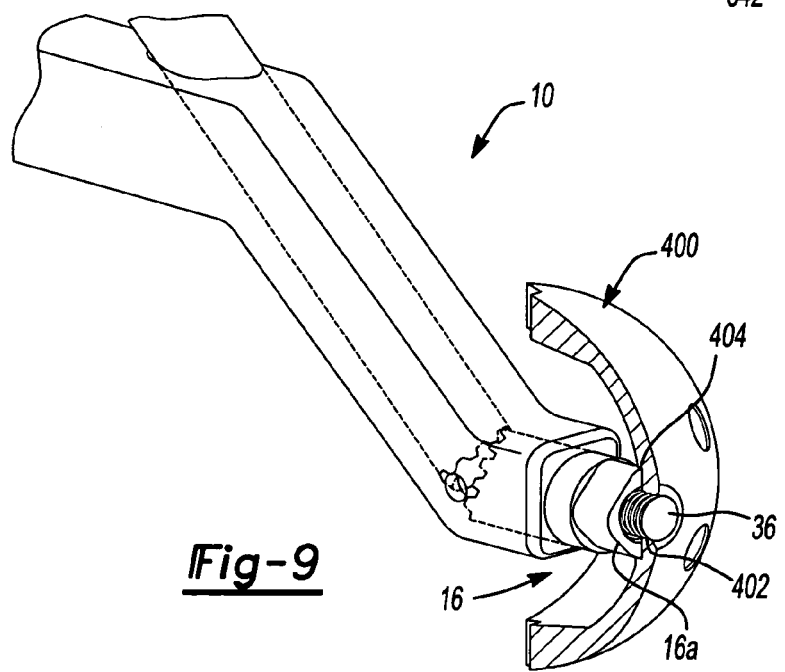
FIG. 9 is a partial detailed view of the instrument in FIG. 1 affixed to an acetabular implant.

A distal end of the torque transfer portion 338 may define a plurality of threads 344 that may be able to engage an implant, such as the implant 400 (FIG. 9). In addition, the positioning portion 16 may define an appropriate cross-section, such as square, to allow for an engagement of the implant 400 with the tool 10. Therefore, the tool 10 may be able to engage the implant 400 and disengage the implant 400 at a selected time to allow for an ease of implantation thereof. It will also be understood that the torque transfer mechanism 334 may be driven by hand or an additional tool. In addition, the torque transfer mechanism 334 may also include other portions, such as the spring 46, to allow for an appropriate placement of the force during impaction of the implant.

Figure 10:
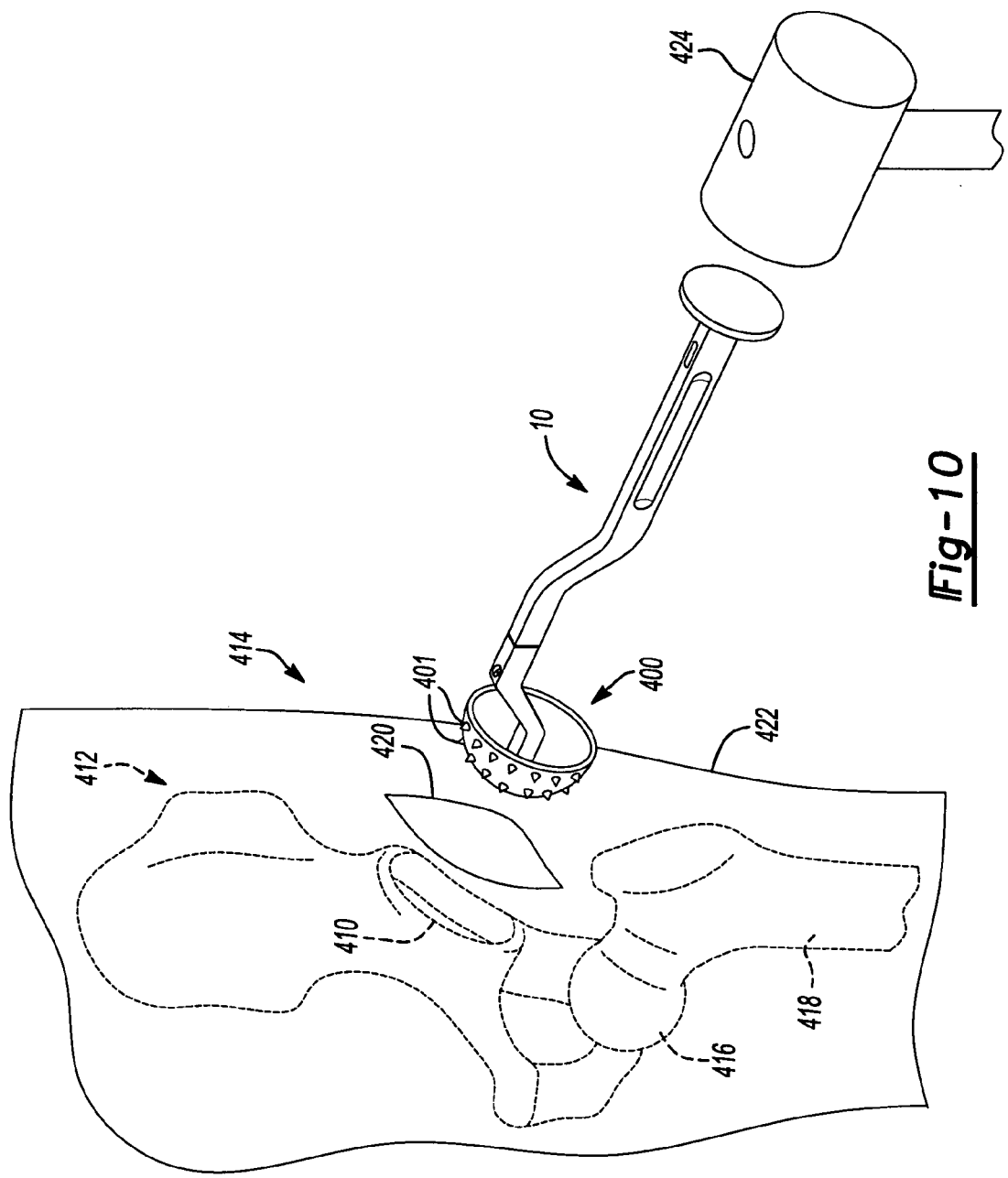
FIG. 10 is an environmental view of a use of the instrument according to an embodiment.
Figure 11:
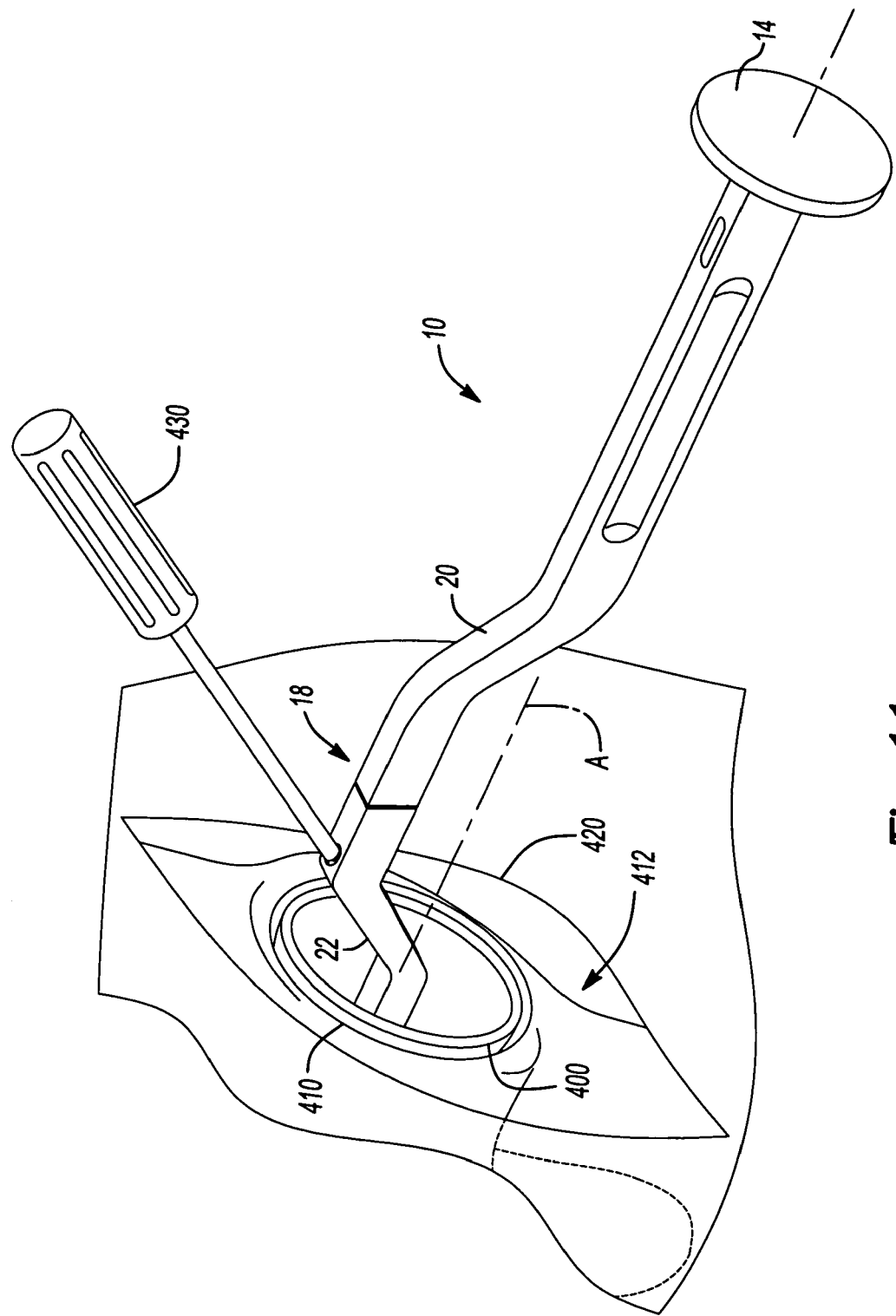
FIG. 11 is a detailed view of the environmental view of FIG. 10.

With reference to FIGS. 9-11 an exemplary embodiment of using the impactor 10 is illustrated. With initial reference to FIG. 9, an acetabular cup 400 is first positioned or fixed relative to the positioning portion 16. The threaded member 36 of the impactor 10 is able to engage an aperture 402 defined by the acetabular cup 400. The aperture 402 generally defines internal threads that are able to engage the external threads of the threaded member 36. Although it will be understood that providing threads is not a necessity. Also, a friction fit or other appropriate interconnection between the acetabular cup 400 and the impactor 10 may be allowed. The threads in the aperture 402, however, may assist in securely and selectively holding the cup 400 during the implant procedure.

Positioning portion 16 may also define a spaced member or a spaced distal portion 16a that may engage a recess or a pocket 404 defined by the acetabular cup 400. Generally, the distal portion of the positioning member 16a allows for an interference fit with the pocket 404. For example, the distal portion 16a may be formed in a square, or any other appropriate shape, such that it may engage the pocket 404 in a manner such that torque or position of the instrument 10 may be transferred to the acetabular cup 400. Nevertheless, it will be understood that the distal portion 16a may be formed in any appropriate shape, such as a hexagon, or other appropriate polygon, or even a cylindrical shape. Simply providing a square is only exemplary of any appropriate shape.

When the threads are provided in the aperture 402 the torque transfer mechanism 24 is used to provide torque to the threaded member 36 to allow the threaded member 36 to engage the threads defined in the aperture 402 of the acetabular cup 400. Therefore, the impactor 10 may be selectively affixed to the acetabular cup 400 prior to attempting to implant the acetabular cup 400 into a prepared acetabulum 410 of a pelvis 412.

Turning reference to FIG. 10, a hip joint 414 of a patient generally includes the pelvis 412 that defines the acetabulum 410. Generally, a femoral head 416 of a femur 418 articulates with the acetabulum 410. In preparation for the procedure, the femoral head 416 may be dislocated from the acetabulum 410. An incision 420 may be formed, through a dermis 422 adjacent the hip joint 414. The incision 420 may be a single incision or may include a plurality of incisions before applying the procedure. Nevertheless, the incision 420 may be a substantially less invasive incision and generally be about 1 cm to about 20 cm. Any appropriate length of the incision 420 may be provided.

The acetabulum 410 may be prepared to receive the cup 400. Preparation of the acetabulum 410 may proceed according to any appropriate or generally known procedure. Also, generally known instruments may be used to prepare the acetabulum 410 for receiving the acetabular cup 400. The preparation need not be any particular preparation, simply to allow the acetabulum 410 to receive the acetabular cup 400 according to a selected procedure. Therefore, preparation for the acetabulum 410 may include reaming the acetabulum for receiving a bone cement mantle to cement the acetabular cup 400 in the selected position or prepared for receiving a plurality of screws or other appliances to hold the acetabular cup 400 in the acetabulum 410.

Once the acetabulum 410 is prepared, the impactor 10 with the acetabular cup 400 affixed thereto can be passed, at least a portion of the impactor 10, through the incision 420. With reference to FIG. 10, the acetabular cup 400 is impacted into the prepared acetabulum 410. An instrument such as a mallet 424 may be used to strike the strikeable portion 14 of the impactor 10 to impact the acetabular cup 400 into the prepared acetabulum. The acetabular cup 400 may also include a spike 401 or other appropriate temporary or permanent fixation means to hold the acetabular cup 400 into the prepared acetabulum 410. Therefore, impacting the impactor 10 with the mallet 424 allows the spikes 401 to engage the prepared acetabulum 410. In addition, a substantial interference fit may be formed between the prepared acetabulum 410 and the acetabular cup 400 such that spikes 401 or other mechanisms are not necessary to affix, either permanently or temporarily, the acetabular cup 400 into the prepared acetabulum 410.

With reference to FIG. 11, after the acetabular cup 400 has been impacted into the prepared acetabulum 410, the impactor 10 is then removed from the acetabular cup 400 using the torque transfer system 24, as described above. To remove impactor 10 from the acetabular cup 400, the instrument 430 is used to engage the torque transfer system 24. Generally, the torque transfer system 24 includes an instrument engageable portion such that the instrument 430, such as a hex driver, may engage the torque transfer system 24 to rotate the threaded portion 36 to disengage the impactor 10 from the acetabular cup 400. As illustrated exemplary in FIG. 11, the angle of the distal extension portion 22 and because the distal extension portion 22 extends away from the alignment axis A, the instrument 430 is substantially not aligned with the acetabular cup 400. This may allow for a substantially unobstructed view of the cup 400.

Having the instrument 430 generally offset or unaligned with the axis A allows for a clear view of the acetabular cup 400. Not only does this assist in the removal of the impactor 10 from the acetabular cup 400, it also assists in providing the acetabular cup 400 into the prepared acetabulum 410. That is, the instrument can be unaligned with the acetabular cup 400 such that the user, such as a physician, can substantially view the acetabular cup 400 through a small incision to ensure proper implantation thereof.

Also during the disengagement of the impactor 10 from the acetabular cup 400, the user, such as the physician, is able to continue to have a generally unobstructed view of the acetabular cup 400. Because the instrument 430 is unaligned with the axis A, the instrument 430 does not obstruct the view of the acetabular cup 400. Nevertheless, the instrument 430 is able to disengage the impactor 10 from the acetabular cup 400 to continue the procedure of implanting a prosthetic system.

Also the generally narrow width of the impactor 10 allows for viewing of the acetabular cup 400 during the implantation procedure. Therefore, the user can ensure the proper alignment and implantation of the acetabular cup 400 into the prepared acetabulum 410. In addition, the incision 420 can be kept to a minimum yet still allowing a physician the clearance and viewing necessary to ensure a proper implantation of the acetabular cup 400.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An instrument for implanting a prosthetic into a selected portion of a body, comprising:
    a prosthetic engaging portion operable to selectively engage the prosthetic and extending along a first axis;
    a graspable portion extending from said prosthetic engaging portion; and
    a rotatable torque transfer system to transfer rotational torque from a second axis to said first axis, said torque transfer system rotates independently of said graspable portion;
    wherein said first axis intersects said second axis;
    wherein said torque transfer system includes at least a first portion extending along said first axis and extending from said prosthetic engaging portion and a second portion extending along said second axis;
    wherein said prosthetic engaging portion is operable to at least one of engage and disengage the prosthetic via said torque transfer system.

2. The instruments of claim 1, further comprising:
    an extending portion extending from said prosthetic engaging portion and operable with said torque transfer system;
    wherein said extending portion extends at an angle relative to said prosthetic engaging portion and substantially defines said second axis.

3. The instrument of claim 1, wherein said prosthetic engaging portion includes a rotatable threaded member;
    wherein said torque transfer system is able to transfer a torque to said rotatable threaded member to rotate said rotatable threaded member to at least one of engage and disengage the prosthetic.

4. The instrument of claim 1, further comprising:
    a strikeable portion;
    wherein said strikeable portion extends from said graspable portion to be struck by a selected instrument;
    wherein said graspable portion extends along said first axis.

5. The instrument of claim 1, further comprising:
    an acetabular cup operable to be disengaged from said prosthetic engaging portion after implantation into the selected portion of the body.

6. The instrument of claim 1, further comprising:
    an intermediate portion generally parallel to said first axis and spaced therefrom; and
    an extending member extending from at least one of said prosthetic engaging portion and said graspable portion to substantially interconnect said intermediate portion and the at least one of said prosthetic engaging portion and said graspable portion.

7. The instrument of claim 1, wherein said prosthetic engaging portion is disposed distally from said graspable portion.

8. The instrument of claim 7, wherein said prosthetic engaging portion is positionable through an incision formed in a dermas while said graspable portion extends to an exterior of the dermas, such that the prosthetic engaging portion is manipulatable with said graspable portion while said prosthetic engaging portion is internally disposed relative to the dermas.

9. The instrument of claim 7, wherein said torque transfer system is disposed adjacent to said prosthetic engaging portion near a distal end of the instrument;
    wherein said torque transfer system is disposed a distance from said graspable portion.

10. The instrument of claim 9, further comprising:
    a torqueing instrument positionable relative to said torque transfer system to provide torque to said torque transfer system;
    wherein said torqueing instrument is positioned near a distal end of the instrument.

11. An apparatus for providing an implant to a selected area of a body, comprising:
    a graspable portion able to transfer a force to an implant engaging portion along a first axis;
    an intermediate portion interconnecting said graspable portion and said implant engaging portion, wherein at least a portion of said intermediate portion is spaced a distance from said first axis;
    an angled portion of said intermediate portion extends along a second axis that intersects said first axis;
    a torque transfer system at least partially housed in said angled portion that rotates independently of said angled portion and transfers rotational torque to said implant engaging portion;
    wherein said torque transfer system is operable to torque said implant engaging portion to at least one of engage and disengage the implant.

12. The apparatus of claim 11, further comprising:
    a strikeable portion;
    wherein said strikeable portion may be struck to apply a force through said implant engaging portion substantially along said first axis to implant the implant.

13. The apparatus of claim 11, wherein said intermediate portion includes a parallel member;
    wherein said parallel member is substantially parallel with said first axis and spaced a distance from said first axis to provide a clear view of said implant engaging portion during use of the apparatus.

14. The apparatus of claim 11, wherein said angled portion extends to allow a tool to engage said torque transfer system while providing a substantially clear view of said implant engaging portion.

15. The apparatus of claim 11, wherein said torque transfer system is operable to transfer torque around an angle defined by said angled portion relative to said implant engaging portion while providing a substantially clear view of said implant engaging portion.

16. The apparatus of claim 15, wherein said torque transfer system is selected from the group including a flexible member, a universal ball joint, an elbow joint, a transverse head tool, and a geared interconnection, a mitre gear, and combinations thereof.

17. The apparatus of claim 11, wherein said implant engaging portion includes a threaded member that is operable to be torqued with said torque transfer system;

wherein said threaded member is able to engage a selected portion of the implant during an implanting procedure.

18. The apparatus of claim 11, wherein said graspable portion is positioned proximally from said implant engaging portion;

wherein said implant engaging portion may be positioned through a dermas of the body while said graspable portion is positioned exterior to said dermas.

19. The apparatus of claim 18, wherein said torque transfer system is positioned substantially adjacent to said implant engaging portion.

20. The apparatus of claim 19, further comprising:

a torque supplying instrument;

wherein said torque supplying instrument can supply a torque to said torque transfer system;

wherein said torque supplying instrument may be positioned distally from said graspable portion.

21. An apparatus for implanting a prosthetic into a selected portion of a body comprising:

a prosthetic holding portion extending along a first axis, said prosthetic holding portion including an outer housing;

a graspable portion extending along said first axis;

a clearance portion between said prosthetic holding portion and said graspable portion, said clearance portion extending along a second axis that is offset from said first axis to provide a user of said apparatus with a clear view of said prosthetic holding portion; and a rotational torque transfer system including a torque transferring portion at said prosthetic holding portion that rotates independently of said outer housing and a driving portion extending from said prosthetic holding portion to said clearance portion, said torque transferring portion is angled relative to said driving portion;

wherein said torque transfer system applies rotational torque to said implant to engage and disengage said implant.

22. The apparatus of claim 21, wherein said torque transferring portion further comprises threads.

23. The apparatus of claim 22, wherein said threads cooperate with threads of said implant.

24. The apparatus of claim 21, wherein said torque transferring portion further comprises first teeth and said driving portion further comprises second teeth; and wherein said first teeth cooperate with said second teeth to transfer torque between said torque transferring portion and said driving portion.

25. The apparatus of claim 21, further comprising a strikable head at said graspable portion.

26. The apparatus of claim 21, wherein a portion of said torque transferring portion extends beyond a surface of said clearance portion, and said clearance portion that extends along said second axis is substantially parallel to said first axis.

27. The apparatus of claim 21, further comprising a first angled portion between said clearance portion and said prosthetic holding portion and a second angled portion between said clearance portion and said graspable portion.

28. The apparatus of claim 27, wherein said driving portion extends through said first angled portion, said driving portion rotates independently of said first angled portion.

* * * * *